(12) United States Patent
Harding

(10) Patent No.: US 7,587,026 B2
(45) Date of Patent: Sep. 8, 2009

(54) SYSTEMS AND METHODS FOR DETERMINING A PACKING FRACTION OF A SUBSTANCE

(75) Inventor: Geoffrey Harding, Hamburg (DE)

(73) Assignee: General Electric Company, Schenectady, NY (US)

( * ) Notice: Subject to any disclaimer, the term of this patent is extended or adjusted under 35 U.S.C. 154(b) by 203 days.

(21) Appl. No.: 11/434,486

(22) Filed: May 15, 2006

(65) Prior Publication Data

US 2007/0263772 A1 Nov. 15, 2007

(51) Int. Cl.
*G01N 23/201* (2006.01)
*G01N 23/20* (2006.01)
(52) U.S. Cl. .......................... 378/88; 378/70
(58) Field of Classification Search ............ 378/57, 378/70, 71, 86–90, 53, 19, 83
See application file for complete search history.

(56) References Cited

U.S. PATENT DOCUMENTS 5,265,144 A 11/1993 Harding et al.

2004/0227822 A1* 11/2004 Cartlidge et al. ....... 348/207.99

OTHER PUBLICATIONS

U.S. Appl. No. 11/434,431, filed May 15, 2006, Geoffrey Harding.
U.S. Appl. No. 11/504,263, filed Aug. 15, 2007, Geoffrey Harding.
U.S. Appl. No. 11/498,114, filed Aug. 2, 2006, Geoffrey Harding.
U.S. Appl. No. 11/498,113, filed Aug. 2, 2006, Geoffrey Harding.
U.S. Appl. No. 11/484,186, filed Jul. 11, 2006, Geoffrey Harding.
U.S. Appl. No. 11/416,526, filed May 3, 2006, Geoffrey Harding.
U.S. Appl. No. 11/541,716, filed Sep. 29, 2006, Geoffrey Harding.
U.S. Appl. No. 11/531,019, filed Sep. 12, 2006, Geoffrey Harding.
U.S. Appl. No. 11/434,291, filed May 15, 2006, Geoffrey Harding.
U.S. Appl. No. 11/504,395, filed Aug. 15, 2006, Geoffrey Harding.
U.S. Appl. No. 11/531,037, filed Sep. 12, 2006, Geoffrey Harding.
Hubbell, J.H., Veigele, W.J., Briggs, E.A., Brown, R.T., Cromer, D.T., Howerton, R.J., "Atomic Form Factors, Incoherent Scattering Functions and Photon Scattering Cross-sections," Journal of Physics and Chemical Reference Data, vol. 4, No. 3, pp. 471-538 (1975).
Hubbell, J.H., Veigele, W.J., Briggs, E.A., Brown, R.T., Cromer, D.T., Howerton, R.J., "Erratum; Atomic Form Factors, Incoherent Scattering Functions, and Photon Scattering Cross Sections," Journal of Physics and Chemical Reference Data, vol. 6, pp. 615-616 (1977).

(Continued)

*Primary Examiner*—Irakli Kiknadze
(74) *Attorney, Agent, or Firm*—Armstrong Teasdale LLP

(57) ABSTRACT

A method for determining a type of a substance is described. The method includes determining a packing fraction of the substance from a molecular interference function.

19 Claims, 9 Drawing Sheets

OTHER PUBLICATIONS

Schlomka et al., "Coherent Scatter Computer Tomography—A Novel Medical Imaging Technique," Physics of Medical Imaging, Proceedings of SPIE—vol. 5030, pp. 256-265 (2003).

Rabiej M., "Determination of the Degree of Crystallinity of Semicrystalline Polymers by Means of the 'OptiFit' Computer Software," Polimery 6, pp. 423-427 (2002).

"Percentage Crystallinity Determination by X-Ray Diffraction," XRD-6000 Application Brief, Kratos Analytical—A Shimadzu Group Company, pp. 1-5 (1999).

A.M. Hindeleh and D. J. Johnson, "The Resolution of Multipeak Data in Fibre Science," J. Phys. D: Appl. Phys., vol. 4. Printed in Great Britain, pp. 259-263 (1971).

\* cited by examiner

US 7,587,026 B2

SYSTEMS AND METHODS FOR DETERMINING A PACKING FRACTION OF A SUBSTANCE

BACKGROUND OF THE INVENTION

This invention relates generally to systems and methods for determining a type of substance and more particularly to systems and methods for determining a packing fraction of the substance.

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. However, existing x-ray baggage scanners, including computed tomography (CT) systems, designed for detection of explosive and illegal substances are unable to discriminate between harmless materials in certain ranges of density and threat materials like plastic explosive.

A plurality of identification systems based on a plurality of x-ray diffraction (XRD) techniques provide an improved discrimination of materials compared to that provided by the x-ray baggage scanners. The XRD identification systems measure a plurality of d-spacings between a plurality of lattice planes of micro-crystals in materials.

However, the XRD identification systems for explosives detection and baggage scanning are not yet highly developed. Moreover, the diffraction techniques suffer from a false alarm problem for some classes of substances. There are certain types of explosives in which an explosive component cannot be identified by the XRD identification systems and the lack of identification leads to a high false alarm rate.

BRIEF DESCRIPTION OF THE INVENTION

In one aspect, a method for determining a type of a substance is described. The method includes determining a packing fraction of the substance from a molecular interference function.

In another aspect, a processor for determining a type of a substance is described. The processor is configured to determine a packing fraction of the substance from a molecular interference function.

In yet another aspect, a system for determining a type of substance is described. The system includes an x-ray source configured to generate x-rays, a detector configured to receive primary and scattered radiation after the x-rays pass through the substance, and a processor configured to determine a packing fraction of the substance from a molecular interference function.

DETAILED DESCRIPTION OF THE INVENTION

Figure 1:
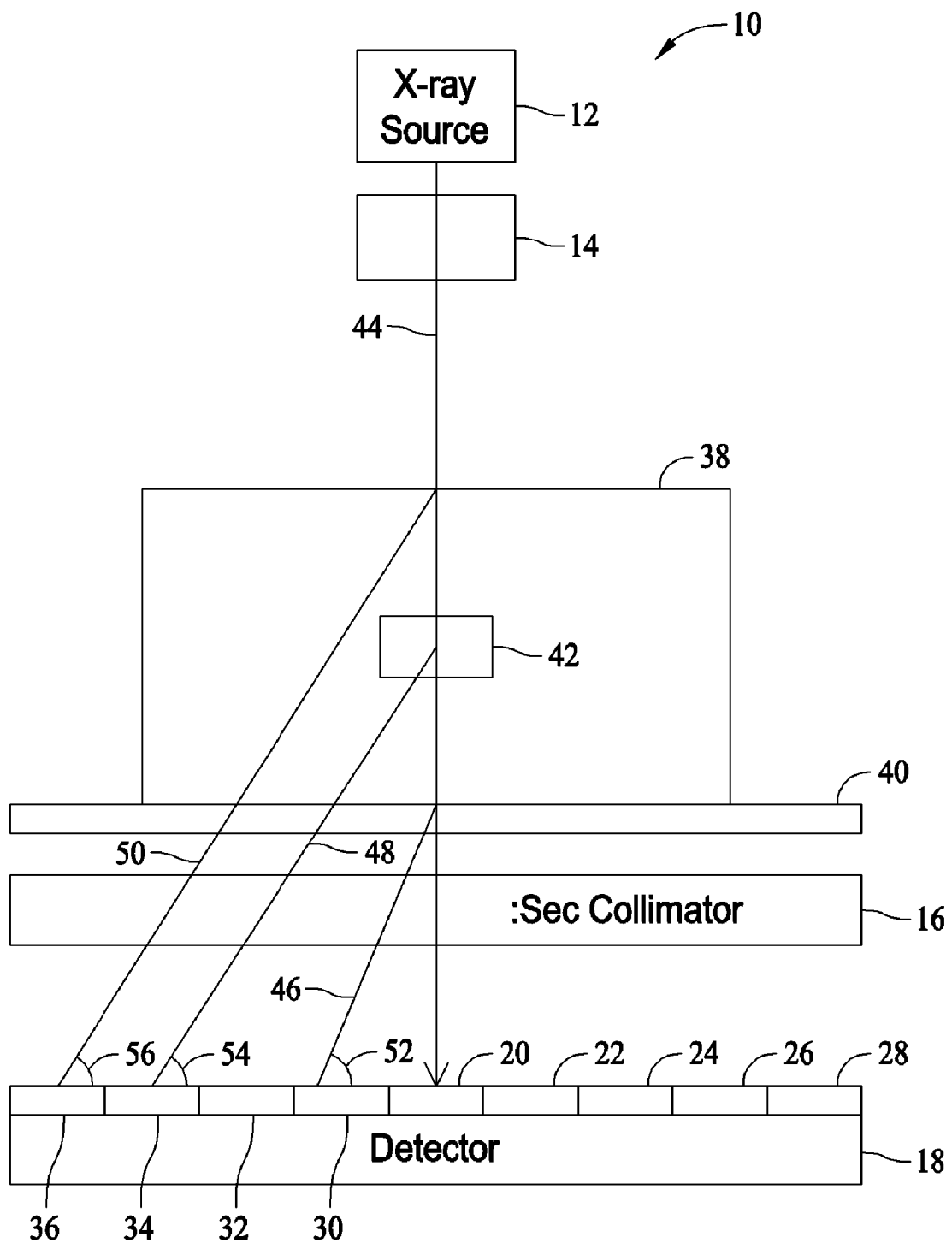
FIG. 1 is a block diagram of a system for determining a packing fraction of a substance.

FIG. 1 is a block diagram of a system 10 for determining a packing fraction of a substance. System 10 includes an x-ray source 12, a primary collimator 14, a secondary collimator (Sec collimator) 16, and a detector 18. Detector 18 includes a central detector element 20 or a central detector cell for detecting primary radiation. Detector 18 also includes a plurality of detector cells or detector elements 22, 24, 26, 28, 30, 32, 34, and 36 for detecting coherent scatter. Detector 18 includes any number, such as, ranging from and including 256 to 1024, of detector elements. A container 38 is placed on a support 40 between x-ray source 12 and detector 18. Examples of container 38 include a bag, a box, and an air cargo container. Examples of x-ray source 12 include a polychromatic x-ray tube. Container 38 includes a substance 42. Examples of substance 42 include an organic explosive, an amorphous substance having a crystallinity of less than twenty five percent, a quasi-amorphous substance having a crystallinity at least equal to twenty-five percent and less than fifty percent, and a partially crystalline substance having a crystallinity at least equal to fifty percent and less than one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 40 include a table and a conveyor belt. An example of detector 18 includes a segmented detector fabricated from Germanium.

X-ray source 12 emits x-rays in an energy range, which is dependent on a voltage applied by a power source to x-ray source 12. Using primary collimator 14, a primary beam 44, such as a pencil beam, is formed from the x-rays generated. Primary beam 44 passes through container 38 arranged on support 40 to generate scattered radiation, such as a plurality of scattered rays 46, 48 and 50. Underneath support 40, there is arranged detector 18, which measures an intensity of primary beam 44 and photon energy of the scattered radiation. Detector 18 measures the x-rays in an energy-sensitive manner by outputting a plurality of electrical output signals linearly dependent on a plurality of energies of x-ray quanta detected from within primary beam 44 and the scattered radiation.

Detector elements 20, 22, 24, 26, 28, 30, 32, 34, and 36 are geometrically arranged so that a scatter angle or alternatively an incident angle of the scatter radiation detected by each detector element 20, 22, 24, 26, 28, 30, 32, 34, and 36 is constant. For example, an incident angle 52 at which scattered ray 46 is incident on detector element 30 is equal to an incident angle 54 at which scattered ray 48 is incident on detector element 34 and incident angle 54 is equal to an incident angle 56 at which scattered ray 50 is incident on detector element 36. As another example, scattered ray 46 is parallel to scattered rays 48 and 50. Central detector element 20 measures an energy or alternatively an intensity of primary beam 44 after primary beam 44 passes through container 38. Detector elements 22, 24, 26, 28, 30, 32, 34, and 36 separately detect the scattered radiation received from container 38.

Secondary collimator 16 is located between support 40 and detector 18. Secondary collimator 16 includes a number of collimator elements, such as sheets, slits, or laminations, to ensure that the scatter radiation arriving at detector 18 have constant scatter angles with respect to primary beam 44 and that a position of detector 18 permits a depth in container 38 at which the scatter radiation originated to be determined. The number of collimator elements provided is equal to or alternatively greater than a number of detector elements 20, 22, 24, 26, 28, 30, 32, 34, and 36 and the collimator elements are arranged such that the scattered radiation between neighboring collimator elements each time is incident on one of the detector elements 22, 24, 26, 28, 30, 32, 34, and 36. The collimator elements are made of a radiation-absorbing material, such as, a copper alloy or a silver alloy. In one embodiment employing a fan-beam geometry, a plurality of origination points, within container 38, of the scatter radiation are detected by the detector elements 22, 24, 26, and 28, aligned in a first direction and detector elements 30, 32, 34, and 36 aligned in a second direction opposite to and parallel to the first direction. Examples of the constant scatter angle values include values ranging from 0.1 degrees for a high-energy device, such as an x-ray tube radiating x-ray photons having an energy of 1 mega electronvolts (MeV) to four degrees for low-energy systems, such as an x-ray tube radiating x-ray photons having an energy of 150 kilo electronvolts (keV). Detector 18 detects the scattered radiation to generate a plurality of electrical output signals. In an alternative embodiment, system 10 does not include primary and secondary collimators 14 and 16.

Figure 2:
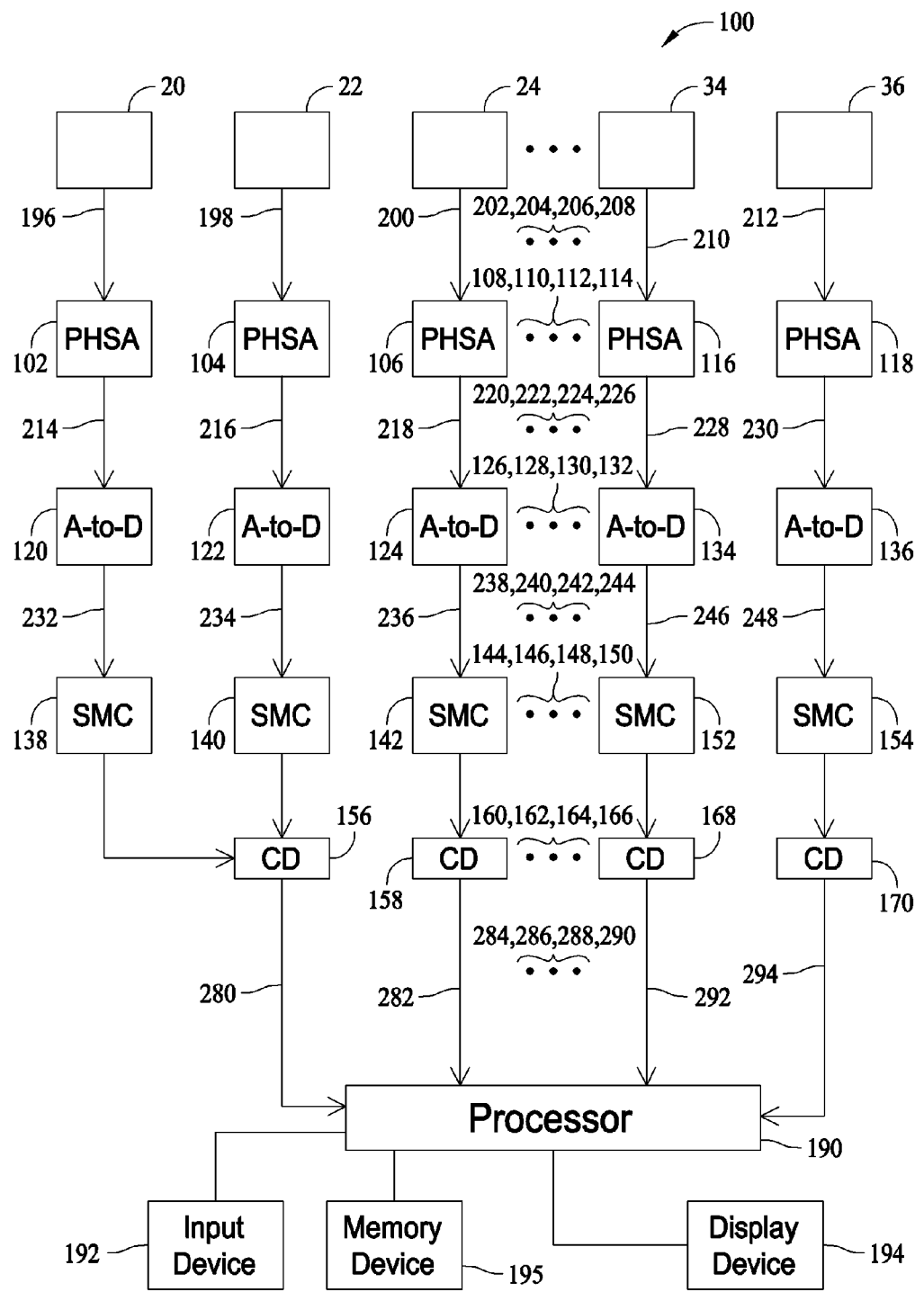
FIG. 2 is a block diagram of an embodiment of the system of FIG. 1.

FIG. 2 is a block diagram of an embodiment of a system 100 for determining a packing fraction of a substance 42. System 100 includes central detector element 20, detector elements 22, 24, 26, 28, 30, 32, 34, and 36, a plurality of pulse-height shaper amplifiers (PHSA) 102, 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for determining a packing fraction of a substance from a computer-readable medium, such as a floppy disk, a compact disc—read only memory (CD-ROM), a magneto-optical disk (MOD), or a digital versatile disc (DVD). In another embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each of correction devices 156, 158, 160, 162, 164, 166, 168, and 170 include a divider circuit. Each of spectrum memory circuits 138, 140, 142, 144, 146, 148, 150, 152, and 154 include an adder and a memory device, such as a RAM or a ROM.

Central detector element 20 is coupled to pulse-height shaper amplifier 102, and detector elements 22, 24, 26, 28, 30, 32, 34, and 36 are coupled to pulse-height shaper amplifiers 104, 106, 108, 110, 112, 114, 116, and 118, respectively. Central detector element 20 generates an electrical output signal 196 by detecting primary beam 44 and detector elements 22, 24, 26, 28, 30, 32, 34, and 36 generate a plurality of electrical output signals 198, 200, 202, 204, 206, 208, 210, and 212 by detecting the scattered radiation. For example, detector element 22 generates electrical output signal 198 for each scattered x-ray photon incident on detector element 22. Each pulse-height shaper amplifier amplifies an electrical output signal received from a detector element. For example, pulse-height shaper amplifier 102 amplifies electrical output signal 196 and pulse-height shaper amplifier 104 amplifies electrical output signal 198. Pulse-height shaper amplifiers 102, 104, 106, 108, 110, 112, 114, 116, and 118 have a gain factor determined by processor 190.

An amplitude of an electrical output signal output from a detector element is proportional to an integrated intensity of an x-ray quantum that is detected by the detector element to generate the electrical output signal. For example, an amplitude of electrical output signal 196 is proportional to an integrated intensity of an x-ray quantum in primary beam 44 detected by detector element 20. On the other hand, an amplitude of electrical output signal 198 is proportional to an integrated intensity of an x-ray quantum within the scattered radiation that is detected by detector element 22.

A pulse-height shaper amplifier generates an amplified output signal by amplifying an electrical output signal generated from a detector element. For example, pulse-height shaper amplifier 102 generates an amplified output signal 214 by amplifying electrical output signal 196 and pulse-height shaper amplifier 104 generates an amplified output signal 216 by amplifying electrical output signal 198. Similarly, a plurality of amplified output signals 218, 220, 222, 224, 226, 228, and 230 are generated. An analog-to-digital converter converts an amplified output signal from an analog form to a digital form to generate a digital output signal. For example, analog-to-digital converter 120 converts amplified output signal 214 from an analog form to a digital format to generate a digital output signal 232. Similarly, a plurality of digital output signals 234, 236, 238, 240, 242, 244, 246, and 248 are generated by analog-to-digital converters 122, 124, 126, 128, 130, 132, 134, and 136, respectively. A digital value of a digital output signal generated by an analog-to-digital converter represents an amplitude of energy or alternatively an amplitude of intensity of a pulse of an amplified output signal. Each pulse is generated by an x-ray quantum, such as an x-ray photon. For example, a digital value of digital output signal 234 output by analog-to-digital converter 122 is a value of an amplitude of a pulse of amplified output signal 216.

An adder of a spectrum memory circuit adds a number of pulses in a digital output signal. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an x-ray examination of substance 42, a memory device within a spectrum memory circuit stores a number of x-ray quanta detected by a detector element. For example, a memory device within spectrum memory circuit 142 stores a number of x-ray photons detected by detector element 24 and each of the x-ray photons has an amplitude of energy or alternatively an amplitude of intensity that is determined by analog-to-digital converter 124.

A correction device receives a number of x-ray quanta that have a range of energies and are stored within a memory device of one of spectrum memory circuits 140, 142, 144, 146, 148, 150, 152, and 154, and divides the number by a number of x-ray quanta having the range of energies received from a memory device of spectrum memory circuit 138. For example, correction device 156 receives a number of x-ray photons having a range of energies from a memory device of spectrum memory circuit 140, and divides the number by a number of x-ray photons having the range received from a memory device of spectrum memory circuit 138. Each correction device outputs a correction output signal that represents a range of energies within x-ray quanta received by a detector element. For example, correction device 156 outputs a correction output signal 280 representing an energy spectrum or alternatively an intensity spectrum within x-ray quanta detected by detector element 22. As another example, correction device 158 outputs correction output signal 282 representing an energy spectrum within x-ray quanta detector element 24. Similarly, a plurality of correction output signals 284, 286, 288, 290, 292, and 294 are generated by correction devices 160, 162, 164, 166, 168, and 170, respectively.

Processor 190 receives correction output signals 280, 282, 284, 286, 288, 290, 292, and 294 to generate a momentum transfer x, measured in inverse nanometers ($nm^{-1}$), from an energy spectrum r(E) of energy E of x-ray quanta within the scattered radiation detected by detector 18. Processor 190 generates the momentum transfer x by applying $$x = (E/hc)\sin(\theta/2) \quad (1)$$

where c is a speed of light, h is Planck's constant, θ represents constant scatter angles of x-ray quanta of the scattered radiation detected by the detector 18. Processor 190 relates the energy E to the momentum transfer x by equation (1). Mechanical dimensions of the secondary collimator 16 define the scatter angle θ. The secondary collimator 16 restricts the scatter radiation that does not have the angle θ. Processor 190 receives the scatter angle θ from a user via input device 192.

It is noted that a number of pulse-height shaper amplifiers 102, 104, 106, 108, 110, 112, 114, 116, and 118 changes with a number of detector elements 20, 22, 24, 26, 28, 30, 32, 34, and 36. For example, five pulse-height shaper amplifiers are used for amplifying signals received from five detector elements. As another example, four pulse-height shaper amplifiers are used for amplifying signals received from four detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Figure 3:
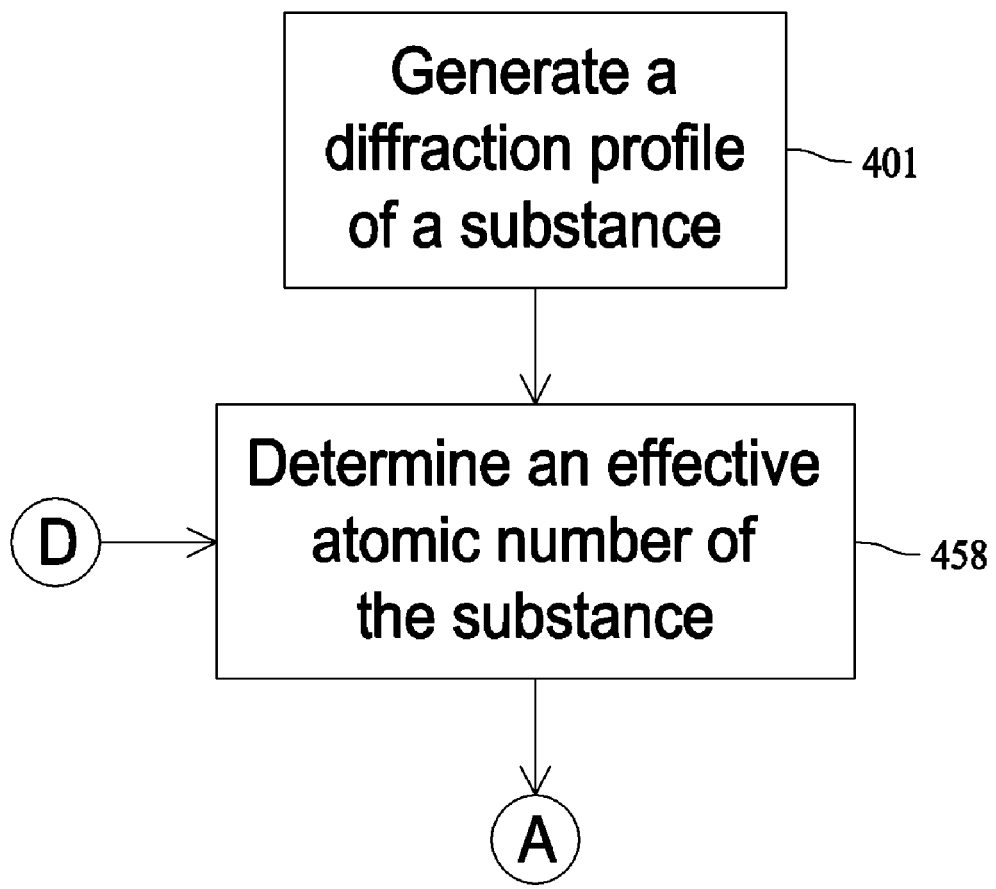
FIG. 3 is a flowchart of an embodiment of a method for determining a packing fraction of a substance.
Figure 4:
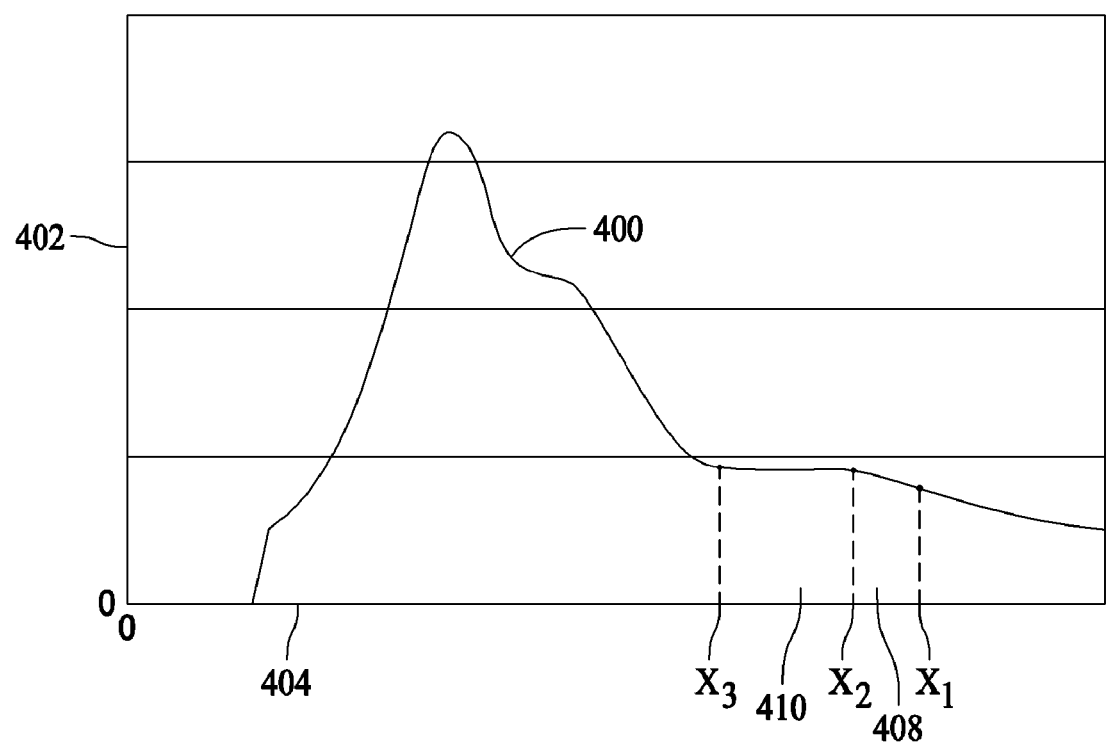
FIG. 4 shows a diffraction profile generated by a processor of the system of FIG. 2.

FIG. 3 is a flowchart of an embodiment of a method for determining a packing fraction of a substance and FIG. 4 shows a graph 400 or a diffraction profile D(x) generated 401 by processor 190. Graph 400 is a histogram having a plurality of intensity values at a plurality of momentum transfer values, such as $x_1$, $x_2$, and $x_3$, of the momentum transfer x. As an example, when an operating voltage of x-ray source 12 is 160 kilovolts, processor 190 calculates, by applying equation 1, an energy value $E_1$ of the energy E to be 160 keV, calculates, by applying equation 1, an energy value $E_2$ of the energy E to be 140 keV, and calculates, by applying equation 1, an energy value $E_3$ of the energy value E to be photon energy 120 keV. In the example, the photon energy values $E_1$, $E_2$, and $E_3$ correspond, through equation 1, to $x_1$ of four inverse nanometers, $x_2$ of 3.5 inverse nanometers, and to $X_3$ of three inverse nanometers, respectively. Graph 400 represents a histogram of a number of x-ray photons detected by detector 18 versus the momentum transfer x of the x-ray photons. A number of photons detected by detector 18 is plotted along an ordinate 402 and the momentum transfer x is plotted along an abscissa 404. As an example, abscissa 404 extends from and includes zero inverse nanometers to at most 10 inverse nanometers. An example of a total number of bins of numbers of x-ray photons plotted on ordinate 402 lies between 64 and 1024. An example of a number of x-ray photons detected by detector 18 per examination lies between 1000 and 100,000.

The diffraction profile ranging from $x \geq 3$ $nm^{-1}$ is dominated by coherent scatter from free atoms of substance 42. In a tip region, extending from $x_1$ to $x_3$, of graph 400, an intensity of the scattered radiation is proportional to a product of density, such as a mean density, of substance 42 and a power, such as ranging between 2.5 and 3.5, of a mean atomic number of a plurality of materials within substance 42.

A cumulative number of photons that are scattered with momentum transfer values between $x_1$ and $x_2$ are represented within a band 408 under graph 400. Processor 190 determines a cumulative number of x-ray photons within band 408 by cumulatively summing a number of photons between momentum transfer values $x_1$ and $x_2$ on abscissa 404. A cumulative number of photons that are scattered with momentum transfer values between $x_2$ and $X_3$ are located within a band 410 under graph 400. Processor 190 determines a cumulative number of x-ray photons within band 410 by cumulatively summing a number of x-ray photons between momentum transfer values $x_2$ and $X_3$ on abscissa 404.

Figure 5:
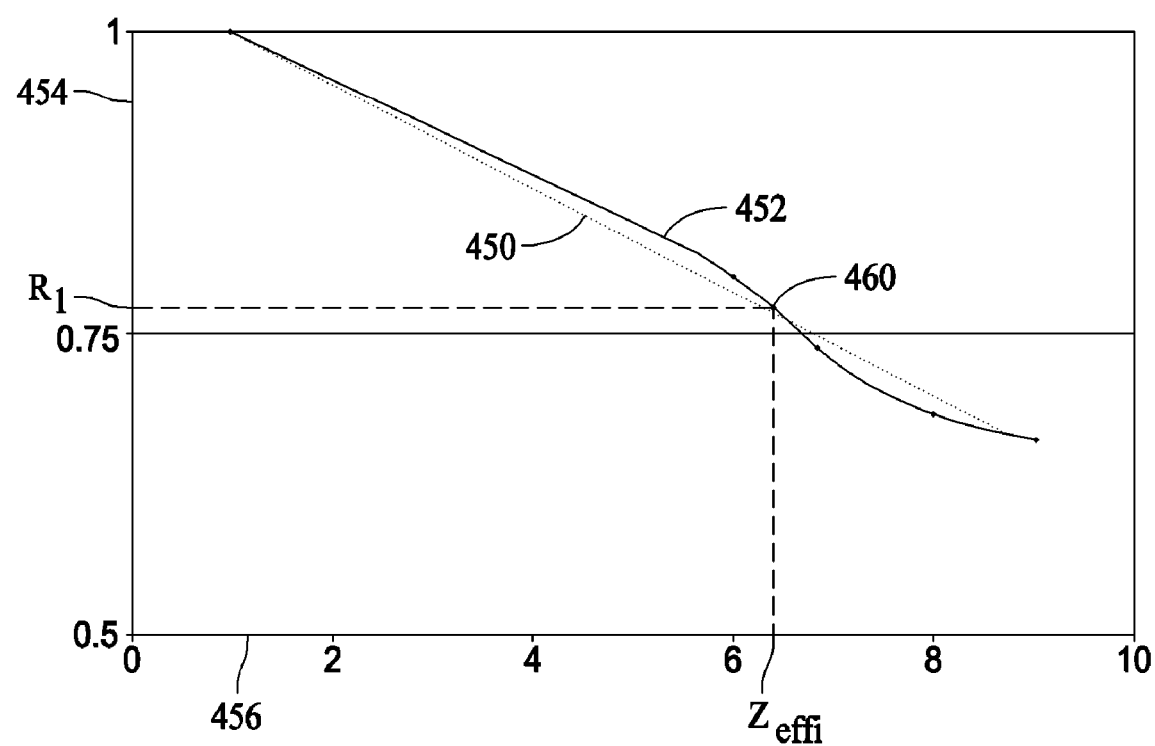
FIG. 5 shows a dotted line and a solid curve generated by the processor of the system of FIG. 2.

FIG. 5 shows a dotted line 450 and a solid curve 452 generated by processor 190. Solid curve 452 represents a theoretical relationship between a ratio of total free atom scatter cross-sections, referred to as total scatter cross-sections or cumulative scatter cross-sections, and an atomic number Z. As an example, processor 190 plots solid curve 452 from an example of the theoretical relationship mentioned in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). As another example, the theoretical relationship includes an atomic number value of oxygen as eight corresponding to a ratio of 0.68 of total scatter cross-sections calculated for oxygen. As yet another example, the theoretical relationship includes an atomic number value of carbon as six corresponding to a ratio of 0.73 of total scatter cross-sections calculated from carbon. As still another example, processor 190 calculates a ratio of a total scatter cross-section of hydrogen at the momentum transfer value $x_3$ and a total scatter cross-section of hydrogen at the momentum transfer value $x_2$, and plots the ratio on solid curve 452. As another example, processor 190 calculates a ratio of a total scatter cross-section of flourine at the momentum transfer value $x_2$ and a total scatter cross-section of flourine at the momentum transfer value $x_1$, and plots the ratio on solid curve 452. As yet another example, processor 190 calculates a ratio of a total scatter cross-section of carbon at the momentum transfer value $x_2$ and a total scatter cross-section of carbon at the momentum transfer value $x_1$, and plots the ratio on solid curve 452. Processor 190 generates dotted line 450 as a linear fit or linear regression to the theoretical relationship.

A plurality of ratios of total scatter cross-sections are plotted along an ordinate 454 and a plurality of atomic numbers Z are measured along an abscissa 456. For example, a plurality of atomic number values on dotted line 450 extend from an atomic number one of hydrogen to an atomic number nine of flourine and a plurality of ratios of total scatter cross-sections evaluated at momentum transfer values within a first set of regions of bands 408 and 410 and total scatter cross-sections evaluated at momentum transfer values within a second set of regions of bands 408 and 410.

Processor 190 calculates a ratio of cumulative numbers of x-ray photons within bands 408 and 410. For example, processor 190 determines that $R_1$ is a ratio of a cumulative number of x-ray photons within band 408 to a cumulative number of x-ray photons within band 410. Processor 190 determines 458, by using the solid curve 452, an effective atomic number $Z_{eff}$ corresponding to a ratio of a cumulative number of x-ray photons within band 408 and a cumulative number of x-ray photons within band 410. As an example, processor 190 perpendicularly extends a horizontal line from the ratio $R_1$ to intersect solid curve 452 at an intersection point 460 and extends a line from intersection point 460 to perpendicularly intersect abscissa 456 at an effective atomic number value $Z_{eff1}$. Alternatively, processor 190 determines, by using the dotted line 450, the effective atomic number $Z_{eff}$ corresponding to a ratio of a cumulative number of x-ray photons within band 408 and a cumulative number of x-ray photons within band 410. As an example, processor 190 perpendicularly extends a horizontal line from the ratio $R_1$ to intersect dotted line 450 at an intersection point and extends a line from the intersection point to perpendicularly intersect abscissa 456 at an effective atomic number value $Z_{eff2}$.

Processor 190 determines a type or a kind, such as uranium, carbon, oxygen, or plutonium, of substance 42 based on the effective atomic number $Z_{eff}$, such as $Z_{eff1}$, determined from a ratio of cumulative numbers of x-ray photons. For example, processor 190 determines that substance 42 is carbon upon determining that an effective atomic number value 6 corresponds to a ratio of 0.73 of cumulative numbers of x-ray photons detected by detector 18. Alternatively, processor 190 determines a type or a kind, such as uranium, carbon, oxygen, or plutonium, of substance 42 based on the effective atomic number value $Zeff_2$ determined from a ratio of cumulative numbers of x-ray photons.

Figure 6:
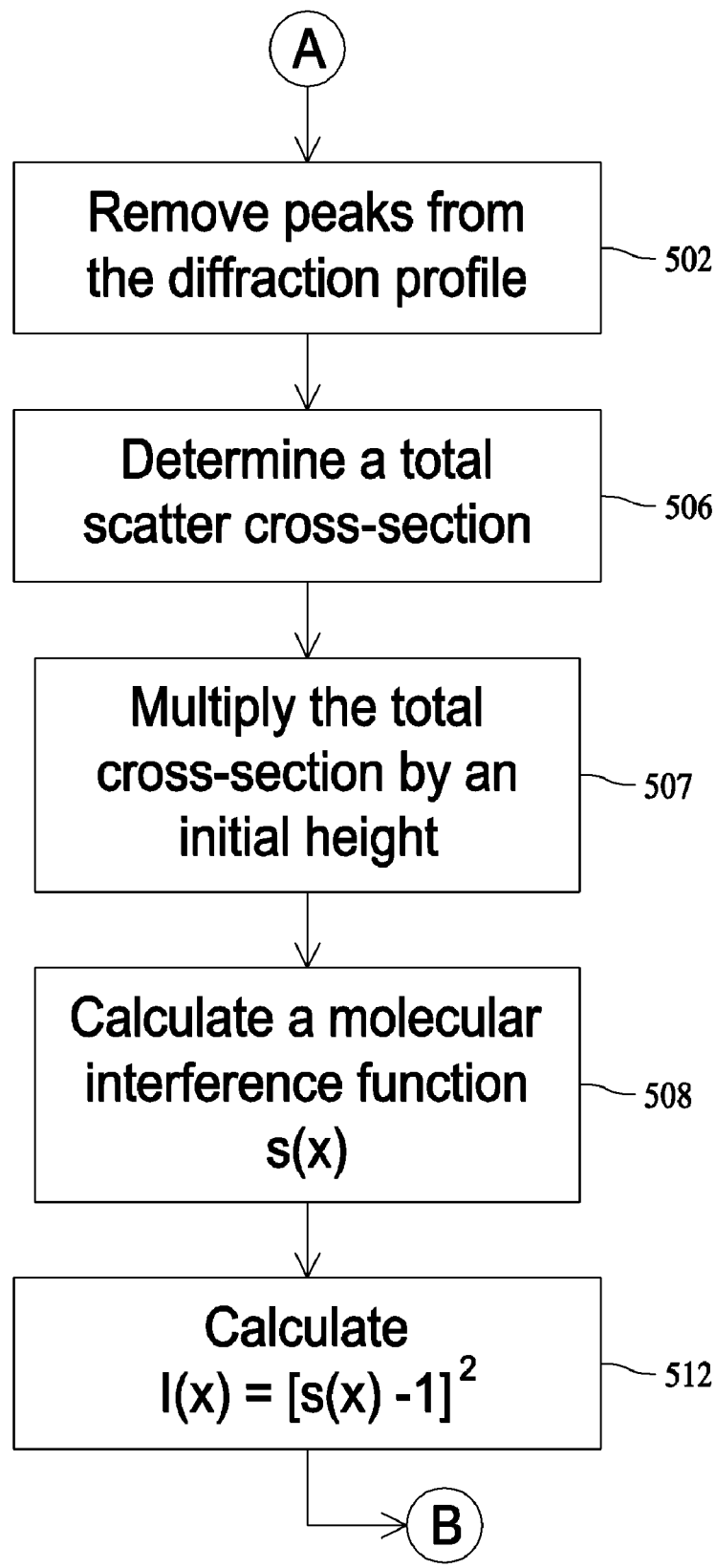
FIG. 6 is a continuation of the flowchart of FIG. 3.
Figure 7:
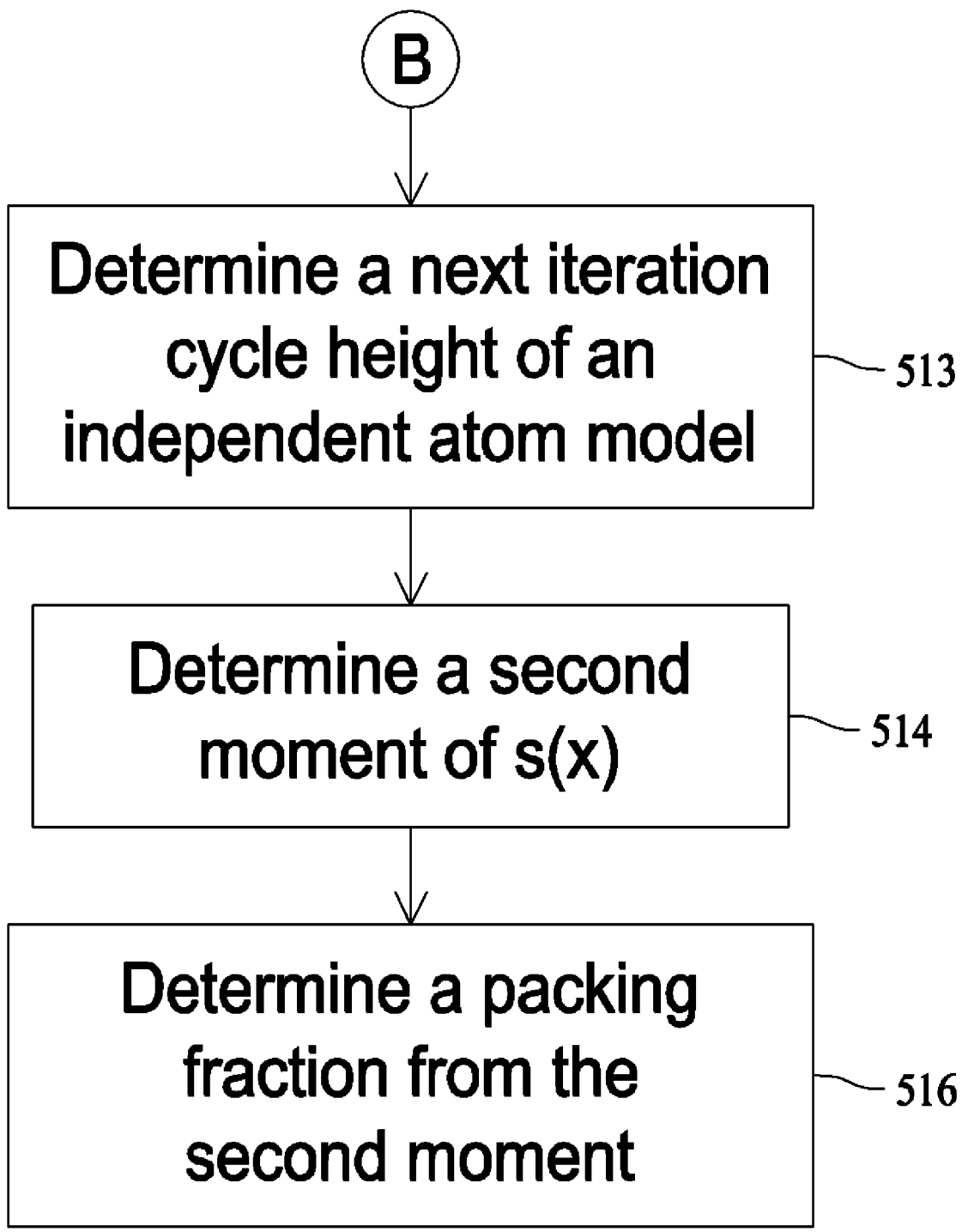
FIG. 7 is a continuation of the flowchart of FIG. 6.
Figure 8:
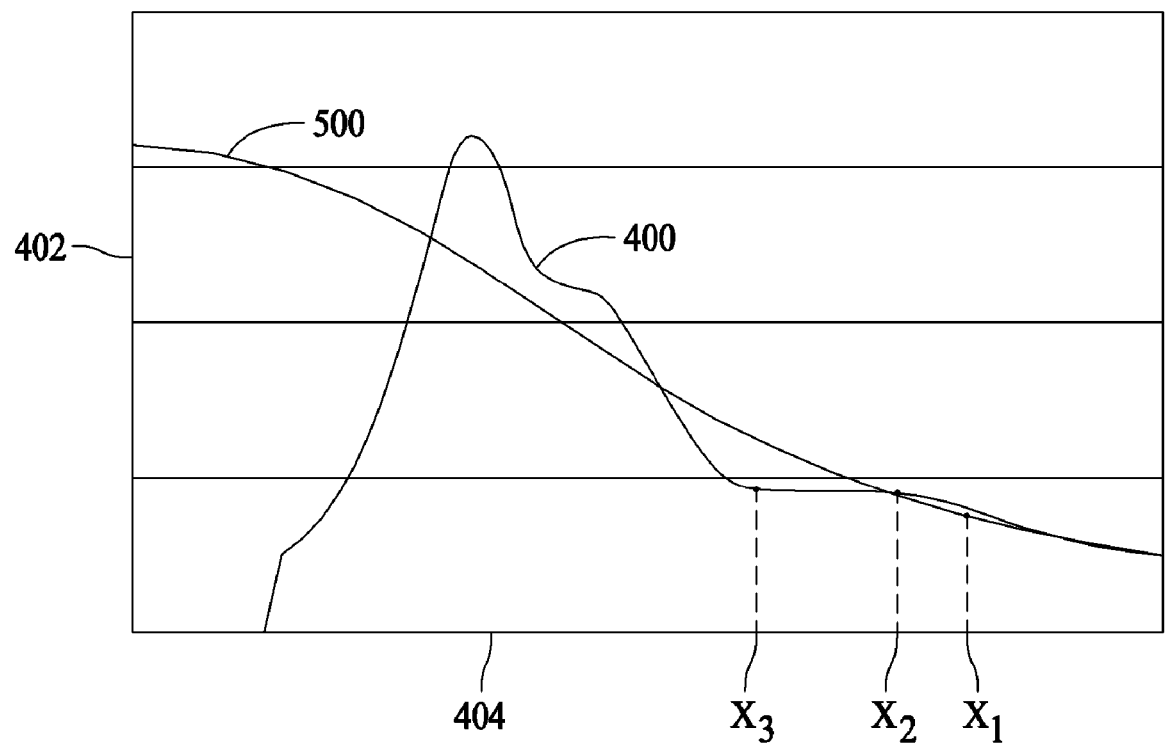
FIG. 8 shows an independent atom model curve generated by applying the method of FIGS. 3, 6 and 7.
Figure 9:
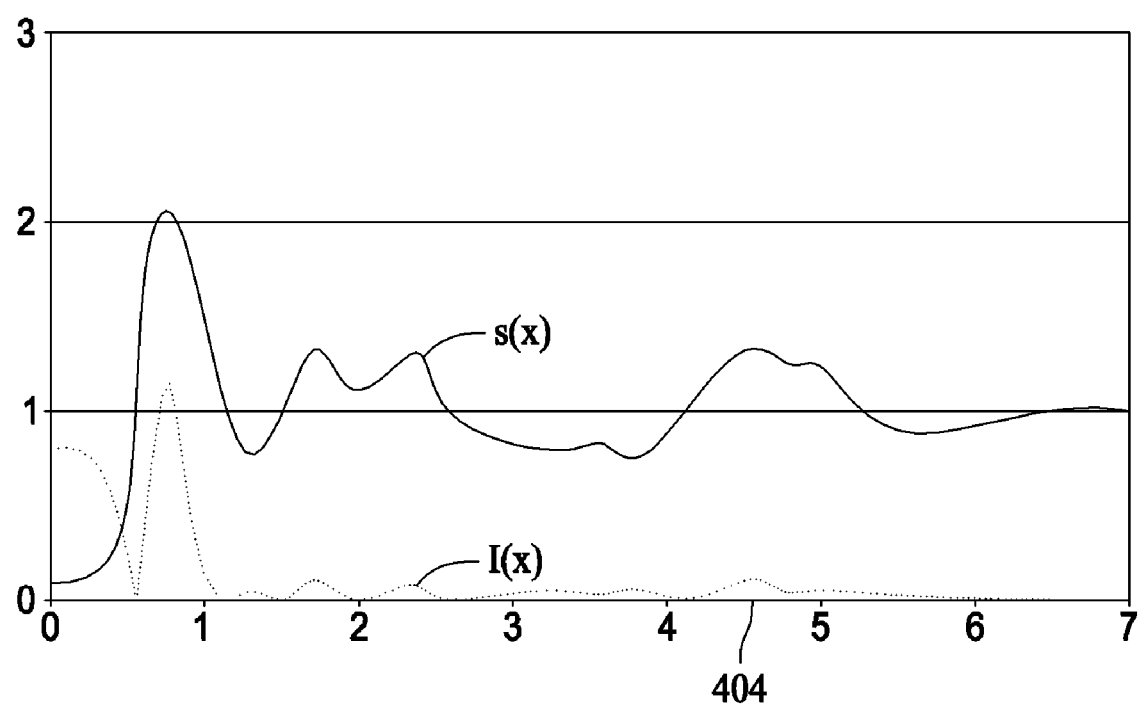
FIG. 9 shows an embodiment of a molecular transfer function and an embodiment of an approximation function generated by applying the method of FIGS. 3, 6 and 7.

FIGS. 6 and 7 are a flowchart of an embodiment of a method for determining a packing fraction of a substance, FIG. 8 shows an embodiment of an independent atom model (IAM) curve 500 generated by processor 190, and FIG. 9 shows a plurality of embodiments of a plurality of graphs s(x) and I(x) generated by processor 190. The graph s(x) represents a molecular interference function and the graph I(x) represents an approximation function. Processor 190 removes 502 a plurality of crystalline interference peaks from graph 400 by applying a peak removal algorithm. An example of the peak removal algorithm is provided in a software, such as an "OptiFit" computer software, described in Rabiej M, Determination of the Degree of Crystallinity of Semicrystalline Polymers by Means of the "OptiFit" Computer Software, POLIMERY 6, pages 423-427 (2002). In an alternative embodiment, processor 190 removes all crystalline interference peaks that represents a crystallinity of substance 42 and that are located within the diffraction profile D(x) by applying the peak removal algorithm. For example, in case of quasi-amorphous or alternatively partially crystalline substances, a plurality of crystalline interference peaks may be included within graph 400 and processor 190 removes the crystalline interference peaks by applying the peak removal algorithm. The peak removal algorithm is applied to generate a peak-removed graph, such as graph 400.

Processor 190 determines 506 a total scatter cross-section of IAM curve 500 from the effective atomic number $Z_{eff}$ that is illustrated in FIG. 5 and that is determined from the scattered radiation. For example, upon determining by processor 190 that the effective atomic number value $Z_{eff1}$ is a rational number, such as 6.3, processor 190 generates a weighted average of a plurality of IAM functions corresponding to neighboring atomic numbers six and seven. In the example, processor 190 generates the weighted average, such as ⅓[IAM(6)]+⅔[IAM(7)], where IAM(6) is a total scatter cross-section for carbon and IAM(7) is a total scatter cross-section for nitrogen. An example of the IAM functions corresponding to neighboring atomic numbers are available in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). The weighted average is an example of a total scatter cross-section, determined in 506, of IAM curve 500.

Alternatively, instead of generating the weighted average, upon determining by processor 190 that the effective atomic number value $Z_{eff1}$ is the rational number, processor 190 generates a closest total scatter cross-section of an IAM curve corresponding to an atomic number value, which is an integer closest to the rational number and plots, with respect to y-axis 402, the closest total scatter cross-section. In yet another alternative embodiment, instead of generating the weighted average, upon determining by processor 190 that the effective atomic number value $Z_{eff1}$ is the rational number, processor 190 generates a universal total scatter cross-section of an IAM curve by scaling the momentum transfer x of IAM curve 500 in FIG. 8. As an example, abscissa 404 in FIG. 8 is scaled by multiplying the momentum transfer x of IAM curve 500 with $0.02Z_{eff1}+0.12$ to generate the universal total scatter cross-section.

Processor 190 multiplies 507 a total scatter cross-section, determined in 506, by an initial amplitude or an initial height to generate a first iteration cycle free atom curve. For example, processor 190 multiplies each value of a total scatter cross-section, determined in 506, with the initial height to generate the first iteration cycle free atom curve. Processor 190 receives the initial height from the user via input device 192. Processor 190 calculates 508 the molecular interference function s(x) by dividing a number of x-ray photons represented by graph 400 by the first iteration cycle free atom curve. As an example, processor 190 generates a molecular interference value $s_1(x)$ of the molecular interference function s(x) by dividing a number of x-ray photons having the momentum transfer value $x_1$ that lies on graph 400 by a number of x-ray photons having the momentum transfer value $x_1$ that lies on the first iteration cycle free atom curve. As another example, processor 190 generates a molecular interference value $s_2(x)$ of the molecular interference function s(x) by dividing a number of x-ray photons having the momentum transfer value $x_2$ that lies on graph 400 by a number of x-ray photons having the momentum transfer value $x_2$ that lies on the first iteration cycle free atom curve.

Processor 190 calculates 512 the approximation function I(x) as $$I(x)=[s(x)-1]2 \qquad (2)$$

Processor 190 determines 513 a next iteration cycle amplitude $I_{min}$ or a next iteration cycle height of IAM curve 500 by minimizing an integral of I(x) represented as $$\int_0^{x_{max}} I(x)\,dx \qquad (3)$$

where $x_{max}$ is the largest value of x on abscissa 404 of graph 400 and IAM curve 500. For example, processor 190 determines the next iteration cycle height $I_{min}$ by selecting a minimum from a first and a second calculated value. Processor 190 determines the first calculated value by applying 507, 508, 512, and equation (3) to the initial height. Processor 190 determines the second calculated value by applying 507, 508, 512, and equation (3) to a changed height instead of the initial height. For example, processor 190 multiplies a total scatter cross-section, determined in 506, by the changed height to generate a second iteration cycle free atom curve, calculates the molecular interference function s(x) by dividing a number of x-ray photons represented by graph 400 by the second iteration cycle free atom curve, calculates the approximation function I(x) from equation (2), and generates the second calculated value by applying equation (3). Processor 190 generates the changed height by modifying, such as incrementing or decrementing, the initial height. As another example, processor 190 determines the next iteration cycle height $I_{min}$ by selecting a minimum from a plurality, such as three, of calculated values, such as the first calculated value, the second calculated value, and a third calculated value. Processor 190 generates the third calculated value in a similar manner in which first and second calculated values are generated. For example, processor 190 generates the third calculated value after incrementing or alternatively decrementing the changed height.

Processor 190 determines 514 a second moment X2S of I(x) by applying $$X2S = \frac{\int_0^\infty x^2 I_{min}(x)\,dx}{\int_0^\infty I_{min}(x)\,dx} \qquad (4)$$

Processor 190 determines 516 a packing fraction η of substance 42 as being linearly proportional, such as equal, to the second moment X2S. The packing fraction η is linearly proportional to the second moment X2S when substance 42 includes a plurality of identical hard spheres. An example of the linearly proportional relationship includes $$\eta = a(X2S) \qquad (5)$$

where a is a coefficient received by processor 190 via input device 192 from the user, a ranges from and including 0.1 to 0.2.

Technical effects of the herein described systems and methods include determining a packing fraction of substance 42 to identify a kind of substance 42. Other technical effects include determining whether substance 42 is a special nuclear material.

While the invention has been described in terms of various specific embodiments, those skilled in the art will recognize that the invention can be practiced with modification within the spirit and scope of the claims.

What is claimed is:

1. A method for determining a type of a substance, said method comprising:
   determining a molecular interference function as a ratio of a measured diffraction profile of the substance and a theoretical total free atom scatter cross-section; and
   determining a packing fraction of the substance from the molecular interference function.

2. A method in accordance with claim 1 further comprising removing a plurality of cryslalline interference peaks from a diffraction profile of the substance before said determining the packing fraction of the substance.

3. A method in accordance with claim 1 wherein the diffraction profile is obtained by receiving scattered x-rays from the substance.

4. A method in accordance with claim 1 further comprising
   generating the theoretical total free atom scatter cross-section based on an effective atomic number of the substance.

5. A method in accordance with claim 1 further comprising calculating a second moment from the molecular interference function.

6. A method in accordance with claim 1 further comprising:
   calculating a second moment from the molecular interference function; and
   generating a packing fraction from the second moment.

7. A processor for determining a type of a substance, said processor configured to:
   determine a molecular interference function as a ratio of a measured diffraction profile of the substance and a theoretical total free atom scatter cross-section; and
   determine a packing fraction of the substance from the molecular interference function.

8. A processor in accordance with claim 7 wherein said processor further configured to remove a plurality of crystalline interference peaks from a diffraction profile of the substance before determining the packing fraction of the substance.

9. A processor in accordance with claim 7 wherein the diffraction profile is obtained by receiving scattered x-rays from the substance.

10. A processor in accordance with claim 7 wherein said processor further configured to
    generate the theoretical total free atom scatter cross-section based on an effective atomic number of the substance.

11. A processor in accordance with claim 7 wherein said processor further configured to calculate a second moment from the molecular interference function.

12. A processor in accordance with claim 7 wherein said processor further configured to:
    calculate a second moment from the molecular interference function; and
    generate a packing fraction from the second moment.

13. A processor in accordance with claim 7 wherein said processor further configured to calculate a second moment from the molecular interference function by applying $$X2S = \frac{\int_0^\infty x^2 I_{min}(x)\,dx}{\int_0^\infty I_{min}(x)\,dx},$$

where X2S is the second moment, x is a momentum transfer, and $I_{min}(X)$ is an iteration cycle amplitude determined from the molecular interference function.

14. A processor in accordance with claim 7 wherein said processor further configured to:
    calculate a second moment from the molecular interfer-ence function; and generate a packing fraction from the second moment by applying η=a(X2S) where η is the packing fraction, X2S is the second moment and a is a coefficient received by the processor.

15. A system for determining a type of substance, said system comprising:
  an x-ray source configured to generate x-rays;
  a detector configured to receive primary and scattered radiation after the x-rays pass through the substance; and
  a processor configured to determine a molecular interference function as a ratio of a measured diffraction profile of the substance and a theoretical total free atom scatter cross-section and determine a packing fraction of the substance from the molecular interference function.

16. A system in accordance with claim 15 wherein said processor further configured to remove a plurality of crystalline interference peaks from a diffraction profile of the substance before determining the packing fraction of the substance.

17. A system in accordance with claim 15 wherein the diffraction profile is obtained by receiving scattered x-rays from the substance.

18. A system in accordance with claim 15 wherein said processor further configured to
  generate the theoretical total free atom scatter cross-section based on an effective atomic number of the substance.

19. A system in accordance with claim 15 wherein said processor further configured to calculate a second moment from the molecular interference function.

* * * * *

UNITED STATES PATENT AND TRADEMARK OFFICE
CERTIFICATE OF CORRECTION

PATENT NO.       : 7,587,026 B2                                      Page 1 of 1
APPLICATION NO.  : 11/434486
DATED            : September 8, 2009
INVENTOR(S)      : Geoffrey Harding It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 319 days.

Signed and Sealed this

Twenty-first Day of September, 2010

David J. Kappos
*Director of the United States Patent and Trademark Office*